(12) United States Patent
Weatherspoon et al.

(10) Patent No.: US 9,892,984 B2
(45) Date of Patent: Feb. 13, 2018

(54) EMBEDDED ELECTRONIC PACKAGING AND ASSOCIATED METHODS

(71) Applicant: HARRIS CORPORATION, Melbourne, FL (US)

(72) Inventors: Michael Raymond Weatherspoon, West Melbourne, FL (US); Louis Joseph Rendek, Jr., Melbourne, FL (US)

(73) Assignee: HARRIS CORPORATION, Melbourne, FL (US)

( * ) Notice: Subject to any disclaimer, the term of this patent is extended or adjusted under 35 U.S.C. 154(b) by 0 days.

(21) Appl. No.: 15/234,094

(22) Filed: Aug. 11, 2016

(65) Prior Publication Data

US 2016/0351459 A1    Dec. 1, 2016

Related U.S. Application Data

(62) Division of application No. 14/023,799, filed on Sep. 11, 2013, now Pat. No. 9,443,789.

(51) Int. Cl.
*H01L 29/40* (2006.01)
*H01L 23/08* (2006.01)
(Continued)

(52) U.S. Cl.
CPC .......... *H01L 23/08* (2013.01); *H01L 21/2885* (2013.01); *H01L 21/486* (2013.01);
(Continued)

(58) Field of Classification Search
CPC . H01L 23/08; H01L 21/2885; H01L 21/4817; H01L 21/486; H01L 21/4864;
(Continued)

(56) References Cited

U.S. PATENT DOCUMENTS 3,903,590 A    9/1975  Yokogawa
4,636,434 A    1/1987  Okamura et al.
(Continued)

FOREIGN PATENT DOCUMENTS

JP    2002231762    8/2002
KR    101253514    4/2013

OTHER PUBLICATIONS

Thompson et al "Packaging of MMICs in Multilayer LCP Substates" IEEE Mocrowave and Wireless Components LEtters, vol. 16, No. 7, Jul. 2006: pp. 410-412.
(Continued)

*Primary Examiner* — Truong Q Dang
*Assistant Examiner* — Patricia Reddington
(74) *Attorney, Agent, or Firm* — Allen, Dyer, Doppelt + Gilchrist, P.A., Attorneys at Law

(57) ABSTRACT

An electronic package includes a semiconductor die, conductive pillars extending outwardly from the semiconductor die, and a liquid crystal polymer (LCP) body surrounding the semiconductor die and having openings therein receiving respective ones of the conductive pillars. A first interconnect layer is on the LCP body and contacts the openings. Conductive bodies are in the openings to connect the conductive pillars to the first interconnect layer.

21 Claims, 3 Drawing Sheets

(51) Int. Cl.
| | |
|---|---|
| *H01L 23/48* | (2006.01) |
| *H01L 21/56* | (2006.01) |
| *H01L 23/29* | (2006.01) |
| *H01L 23/538* | (2006.01) |
| *H01L 23/00* | (2006.01) |
| *H05K 1/18* | (2006.01) |
| *H01L 21/288* | (2006.01) |
| *H01L 21/48* | (2006.01) |
| *H01L 21/52* | (2006.01) |
| *H01L 23/498* | (2006.01) |
| *H01L 23/522* | (2006.01) |
| *A61N 1/375* | (2006.01) |
| *H05K 1/11* | (2006.01) |

(52) U.S. Cl.
CPC ...... *H01L 21/4817* (2013.01); *H01L 21/4864* (2013.01); *H01L 21/52* (2013.01); *H01L 21/56* (2013.01); *H01L 23/293* (2013.01); *H01L 23/481* (2013.01); *H01L 23/49805* (2013.01); *H01L 23/49827* (2013.01); *H01L 23/5226* (2013.01); *H01L 23/5389* (2013.01); *H01L 24/20* (2013.01); *H01L 24/24* (2013.01); *H01L 24/82* (2013.01); *H05K 1/185* (2013.01); *A61N 1/375* (2013.01); *A61N 1/3758* (2013.01); *H01L 2224/04105* (2013.01); *H01L 2224/2402* (2013.01); *H01L 2224/48091* (2013.01); *H01L 2224/48472* (2013.01); *H01L 2224/73265* (2013.01); *H01L 2224/821* (2013.01); *H01L 2224/82039* (2013.01); *H01L 2924/12042* (2013.01); *H01L 2924/1421* (2013.01); *H05K 1/115* (2013.01); *H05K 1/189* (2013.01); *H05K 2201/0141* (2013.01); *H05K 2201/10098* (2013.01); *H05K 2201/10151* (2013.01)

(58) Field of Classification Search
CPC ....... H01L 21/52; H01L 21/56; H01L 23/293; H01L 23/481; H01L 23/49805; H01L 23/49827; H01L 23/5226; H01L 23/5389; H01L 24/20; H01L 24/24; H01L 24/82; H05K 1/185

USPC ....................................................... 257/774
See application file for complete search history.

(56) References Cited

U.S. PATENT DOCUMENTS

| | | |
|---|---|---|
| 5,353,498 A | 10/1994 | Fillion et al. |
| 5,866,952 A | 2/1999 | Wojnarowski et al. |
| 6,396,148 B1 | 5/2002 | Eichelberger et al. |
| 7,972,901 B2 | 7/2011 | Farrell et al. |
| 8,345,433 B2 | 1/2013 | White et al. |
| 2004/0056341 A1* | 3/2004 | Endo ............... H01L 23/50 257/678 |
| 2005/0087356 A1 | 4/2005 | Forcier |
| 2006/0108146 A1 | 5/2006 | Wu et al. |
| 2006/0194428 A1 | 8/2006 | Nanda et al. |
| 2007/0025092 A1 | 2/2007 | Lee et al. |
| 2007/0107932 A1 | 5/2007 | Jauniskis et al. |
| 2008/0179724 A1 | 7/2008 | Gregory |
| 2008/0277775 A1 | 11/2008 | Honer et al. |
| 2009/0085190 A1* | 4/2009 | Simon ............ H01L 21/4832 257/698 |
| 2009/0194428 A1 | 8/2009 | Clarke |
| 2010/0140772 A1* | 6/2010 | Lin ............... H01L 21/486 257/686 |
| 2011/0241215 A1 | 10/2011 | Sankman et al. |
| 2011/0254124 A1 | 10/2011 | Nalla et al. |
| 2012/0069288 A1 | 3/2012 | Das et al. |
| 2012/0181073 A1* | 7/2012 | Rendek, Jr. ....... H05K 1/186 174/258 |
| 2014/0264808 A1 | 9/2014 | Wolter et al. |

OTHER PUBLICATIONS

Mahajan et al., "Emerging Directions for Packaging Technologies" Semiconductor Technology and Manufacturing, vol. 06, Issue 02, May 2002, pp. 1-16.

Casio Computer, in collaboration with CMK board manufacturer, embedding wafer level packages (WLP) into boards (see http://world.casio.com/corporate/news/2006/ewlp.html), pp. 1-2.

* cited by examiner

US 9,892,984 B2

1

EMBEDDED ELECTRONIC PACKAGING AND ASSOCIATED METHODS

FIELD OF THE INVENTION

The present invention relates to the field of packaging electronic components, and more particularly, to packaging an embedded semiconductor die and related methods.

BACKGROUND OF THE INVENTION

The basic purpose of packaging electronic components is to protect the components while at the same time providing electrical interconnections from the components through the package. Manufacturability and protection are key concerns. Due to ongoing market demand, electronic packages are continuously being driven toward smaller sizes and reduced footprints while being environmentally robust. Even though these electronic packages are miniaturized they a still highly functional.

Embedded electronics packaging integration requires dielectric material with compatible processing temperatures, compatible material properties and favorable electrical characteristics. Currently, several embedded technologies have been demonstrated using laminate and polymeric circuit boards.

Intel Corporation has developed a bumpless build-up layer that does not use solder bumps to attach the semiconductor die to the package wires. Build-up layers are grown or built-up around the semiconductor die. The build up layers are usually manufactured separately and then bonded together. An integrated module board (IMB) has been developed by Imbera Electronics OY where the component to be embedded has contact terminals on both sides of the component so that space is saved. General Electric Company has a Chips First Build-Up™ where a solderless process is used. Fraunhofer IZM uses a laminated embedded die "Chip in Polymer" packaging approach based upon standard circuit board equipment and techniques where a semiconductor die is bonded to a substrate, laminated with a dielectric, and linked to external circuitry. Casio Computer Co. Ltd. uses Wafer Level Packaging (WLP) where the package is completed directly on the wafer and then singulated by dicing for assembly. All packaging and testing operations of the dies are replaced by whole wafer fabrication and wafer level testing.

None of the above approaches make use of a liquid crystal polymer material (LCP), which has gained considerable attention since becoming commercially available in 2003. LCP materials have very low moisture permeability and can provide a near-hermetic seal without being relatively thick. Moreover, the dielectric properties of LCP materials do not change upon exposure to moisture.

An LCP package for protecting a semiconductor die is disclosed in the article titled "Packaging of MMICs in Multilayer LCP Substrates" by Thompson et al. As illustrated in FIG. 1, an electronic package 20 includes a semiconductor die 22 embedded between LCP layers 30-42 using a lamination process with a cut-out cavity 50 for the semiconductor die. LCP core layers 30, 34, 38 and 42 are 4 mils thick, whereas LCP bond layers 32, 36 and 40 are 2 mils thick. As discussed in the article, the low melting temperature (285° C.) LCP bond layers 32, 36 and 40 are used to adhere the generally thicker higher melting temperature (315° C.) LCP core layers 30, 34, 38 and 42 to create a homogeneous LCP electronic package 20.

2

Even in view of the above-described technologies, emerging wireless communication and sensor applications require ultra thin, flexible, chemically resistant, near-hermetic and affordable embedded electronic packages. This is particularly so when directed to biomedical sensing and imaging, for example. Consequently, there is still a need improve upon embedding a semiconductor die in an electronic package.

SUMMARY OF THE INVENTION

In view of the foregoing background, it is therefore an object of the present invention to provide a low profile electronic package with an embedded semiconductor die that is relatively straightforward to produce.

This and other objects, features, and advantages in accordance with the present invention are provided by an electronic package comprising a semiconductor die, a plurality of conductive pillars extending outwardly from the semiconductor die, and a liquid crystal polymer (LCP) body surrounding the semiconductor die and having a plurality of openings therein receiving respective ones of the plurality of conductive pillars while leaving respective gaps adjacent to the tops of the conductive pillars. A first interconnect layer may be on the LCP body, and a plurality of conductive bodies may be in the respective gaps to connect the plurality of conductive pillars to the first interconnect layer.

The electronic package may further comprise a second interconnect layer on the LCP body on a side thereof opposite the first interconnect layer. A plurality of conductive vias may extend through the LCP body to connect the first and second interconnect layers.

The LCP body advantageously allows the electronic package to be low profile with high flexibility for application in conformal circuits. The semiconductor die may be near-hermetically sealed, and the dielectric properties of the LCP body remain relatively the same when exposed to moisture. Also, since the LCP package is biocompatible with the human body, the electronic package has a wide range of surgically-implanted applications.

Yet another advantage of the electronic package is that it may be used as a building block for more complex architectures wherein LCP bodies may be stacked one on top of another while still providing electrical interfaces between the semiconductor dies in the stacked layers. This is accomplished without the semiconductor die being in a wire-bond or a flip-chip configuration. Instead, the conductive bodies advantageously connect the conductive pillars to the first interconnect layer after the LCP body has been formed around the semiconductor die, and conductive vias advantageously connect the first and second interconnect layers together. The conductive pillars and the conductive vias may be formed using electroplating. As a result, the electronic package is relatively straightforward to produce at reduced costs.

The LCP body may surround the semiconductor die on all sides thereof and be in continuous contact therewith. In addition, the LCP body may laterally surround each of the conductive pillars and be in continuous contact therewith.

The first interconnect layer, the conductive pillars, and the conductive bodies may each comprise copper, for example. The semiconductor die may comprise a radio frequency (RF) integrated circuit, for example.

Another aspect is directed to a method for making an electronic package comprising providing a semiconductor die having a plurality of outwardly extending conductive pillars, and forming an LCP body surrounding the semiconductor die and having a plurality of openings therein receiving respective ones of the plurality of conductive pillars while leaving respective gaps adjacent tops of the conductive pillars, and with a first interconnect layer on the LCP body. The method may further comprise forming a plurality of conductive bodies in the respective gaps to connect the plurality of conductive pillars to the first interconnect layer.

DETAILED DESCRIPTION OF THE PREFERRED EMBODIMENTS

The present invention will now be described more fully hereinafter with reference to the accompanying drawings, in which preferred embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Figure 1:
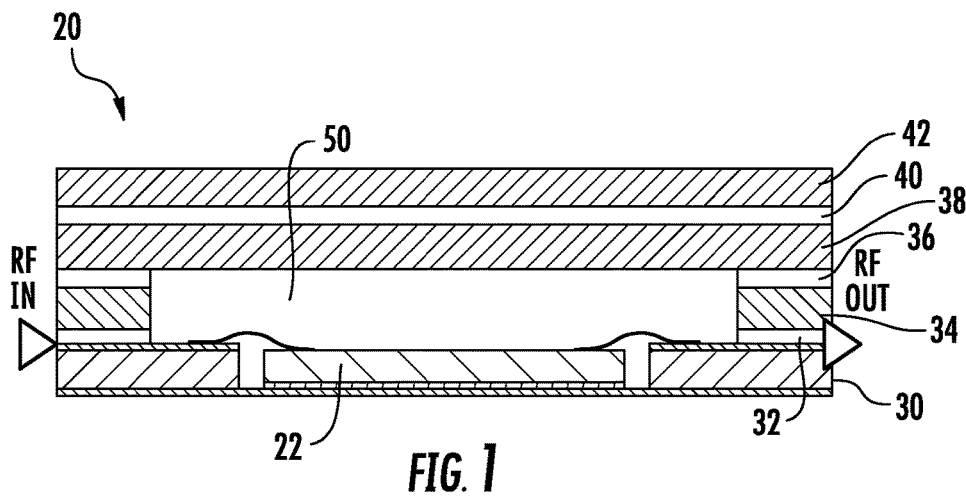
FIG. 1 is a cross-sectional view of an electronic package in accordance with the prior art.
Figure 2:
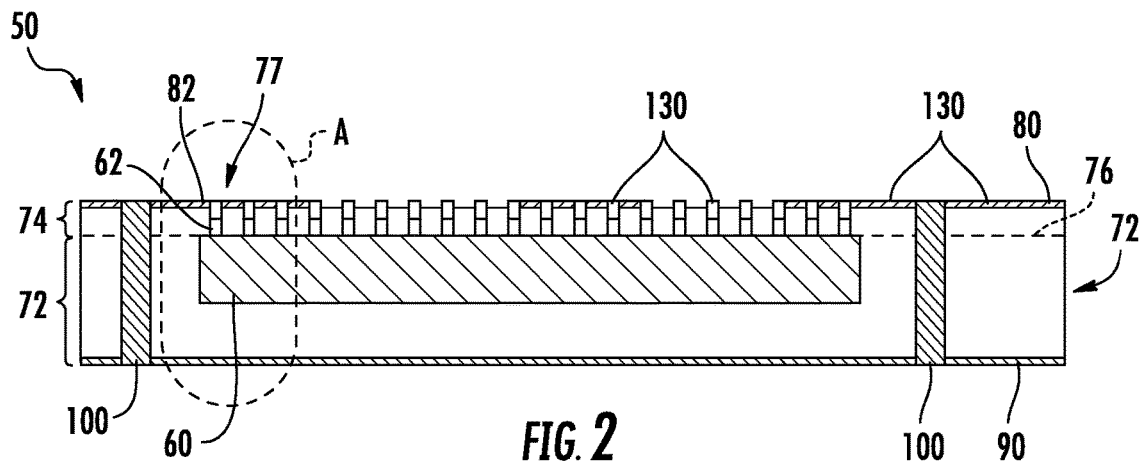
FIG. 2 is a cross-sectional view of an electronic package in accordance with the present invention.
Figure 3:
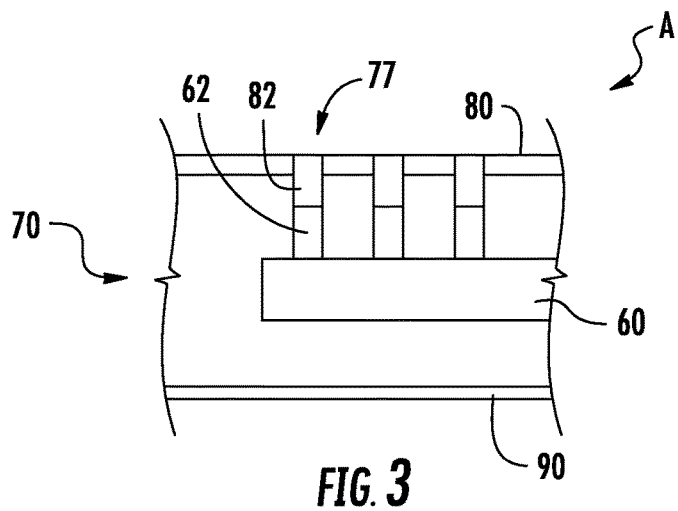
FIG. 3 is an enlarged cross-sectional view of area A in FIG. 2.

Referring initially to FIGS. 2 and 3, an electronic package 50 comprises a semiconductor die 60, a plurality of conductive pillars 62 extending outwardly from the semiconductor die, and a liquid crystal polymer (LCP) body 70 surrounding the semiconductor die 60. The LCP body 70 has a plurality of openings 77 therein receiving respective ones of the plurality of conductive pillars 62 while leaving respective gaps adjacent tops of the conductive pillars. A first interconnect layer 80 is on the LCP body 70. A plurality of conductive bodies 82 is in the respective gaps to connect the conductive pillars 62 to the first interconnect layer 80.

As will be explained in greater detail below, the LCP body 70 includes a first LCP body section 72 and a second LCP body section 74 that is joined with the first LCP body section at a fused interface 76. As an example, an overall thickness of the LCP body 50 may be within a range of 8 to 12 mils. Depending on the thickness of the semiconductor die 60 and the intended application, the thickness of the LCP body 70 will vary accordingly, as readily appreciated by those skilled in the art.

In addition to the electronic package 50 being low profile with high flexibility, the semiconductor die 60 may be near-hermetically sealed and the dielectric properties of the LCP body 70 remain relatively stable when exposed to moisture. Also, since the LCP body 70 is biocompatible with the human body, the electronic package 50 has a wide range of surgically-implanted applications, such as a wireless pacemaker with a physician-accessible remote monitoring system or an implantable retina prosthesis.

The electronic package 50 further includes a second interconnect layer 90 on the LCP body on a side thereof opposite the first interconnect layer 80. Conductive vias 100 extend through the LCP body 70 to connect the first and second interconnect layers 80, 90. This configuration advantageously permits the electronic package 50 to be used as a building block for more complex architectures wherein LCP bodies 70 may be stacked one on top of another while still providing electrical interfaces between the semiconductor dies 60 in the stacked layers. Assembly costs are reduced and the ease of fabrication is improved since electrical interfaces with the semiconductor die 60 are provided without the semiconductor die being in a wire-bond or a flip-chip configuration.

Figure 4:
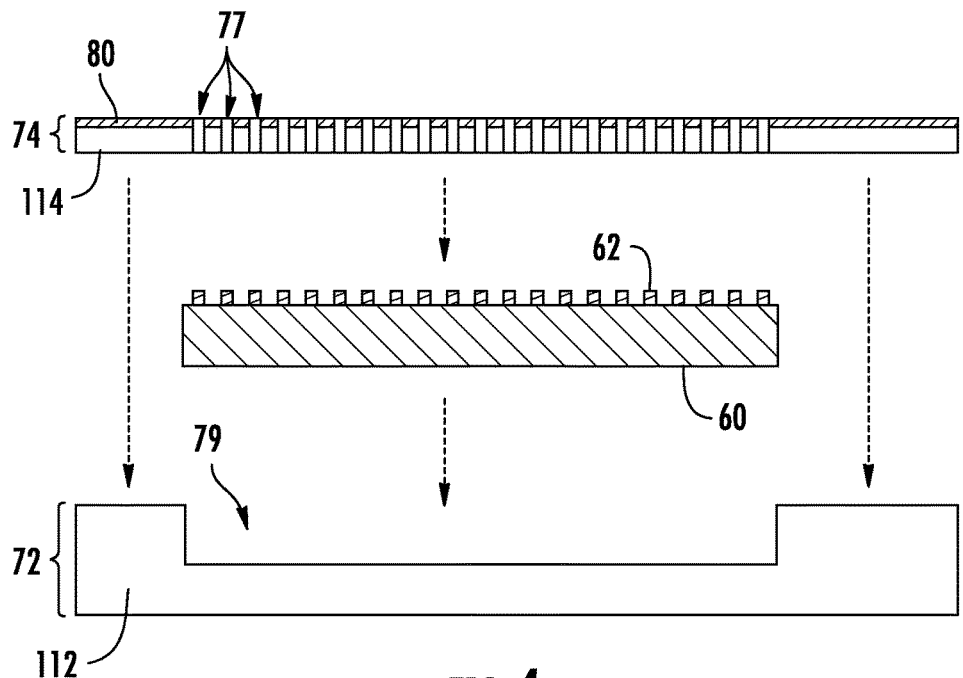
FIG. 4 is an exploded cross-sectional view of the electronic package in FIG. 2 illustrating the first LCP body section having the die receiving cavity, the semiconductor die, and the second LCP body section.
Figure 7:
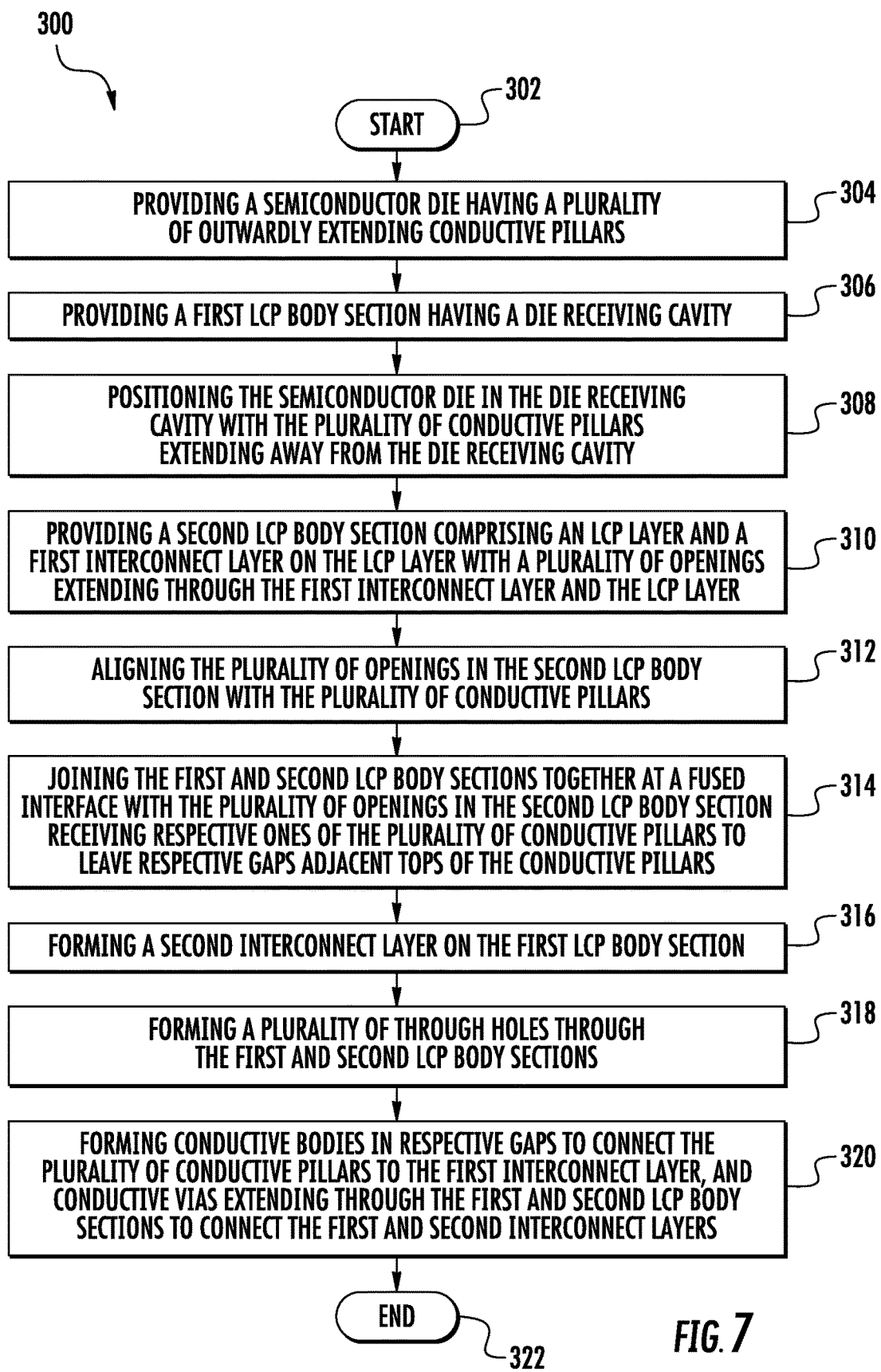
FIG. 7 is a flowchart illustrating a method for making the electronic package illustrated in FIG. 2.

Referring now to the remaining figures, including the flowchart 300 illustrated in FIG. 7, the steps of making the illustrated electronic package 50 will be discussed. From the start (Block 302), a semiconductor die 60 having a plurality of outwardly extending conductive pillars 62 is provided at Block 304 and as illustrated by the exploded view of the electronic package 50 in FIG. 4. The conductive pillars 62 are copper, for example, and are used for alignment and subsequent interconnect purposes. Other metals may be used instead of or along with copper, as readily appreciated by those skilled in the art. The semiconductor die 60 may be a radio frequency (RF) integrated circuit, for example.

The first LCP body section 72 includes a first LCP layer 112 having a die receiving cavity 79 is provided at Block 306. Although the first LCP layer 112 is illustrated as a single LCP layer, multiple LCP layers by be used. The semiconductor die 60 is positioned in the die receiving cavity 79 at Block 308 with the plurality of conductive pillars 62 extending away from the die receiving cavity.

The second LCP body section 74 is provided at Block 310 and includes a second LCP layer 114 and the first interconnect layer 80 is on the second LCP layer with a plurality of openings or vias 77 extending through both the first interconnect layer and the second LCP layer. A laser may be used to form the openings 77. The first interconnect layer 80 is copper, for example. Other metals may be used instead of or along with copper, as readily appreciated by those skilled in the art. As with the first LCP layer 112, the second LCP layer 114 may be formed with single or multiple LCP layers.

Figure 5:
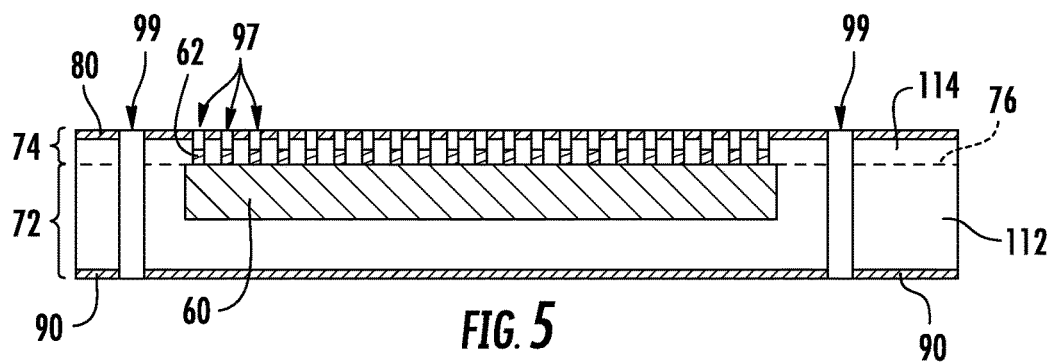
FIG. 5 is a cross-sectional view of the electronic package illustrated in FIG. 2 without the conductive pillars and the conductive vias.

The openings 77 in the second LCP body section 74 are aligned with the conductive pillars 62 at Block 312. The conductive pillars 62 extending outwardly from the semiconductor die 60 are advantageously used for alignment and interconnect purposes. Referring to FIG. 5, the first and second LCP body sections 72, 74 are then joined together at Block 314 with the plurality openings 77 in the second LCP body section receiving respective ones of the conductive pillars 62 to leave respective gaps 97 adjacent tops of the conductive pillars 62. The conductive pillars 62 are thus recessed with in the openings 77.

The first and second LCP body sections 72, 74 are laminated with the semiconductor die 60 included therebetween so that the LCP body 70 surrounds the semiconductor die 60 on all sides thereof and is in continuous contact therewith. Also, the LCP body 70 laterally surrounds each of the conductive pillars 62 and is in continuous contact therewith.

Lamination of the LCP layers 112, 114 in the first and second LCP body sections 72, 74 along with the semiconductor die 60 is achieved within a temperature range of about 285° C. to 315° C., as readily appreciated by those skilled in the art. A fused interface 76, as illustrated in FIG. 5, is formed where the LCP layers 112, 114 are joined together.

A second interconnect layer 90 is formed on the on the LCP layer 112 in the first LCP body section 72 at Block 316 on a side thereof opposite the LCP layer 114 in the second LCP body section 74. The second interconnect layer 90 is also copper. However, other metals may be used instead of or along with copper, as readily appreciated by those skilled in the art. Instead of the second interconnect layer 90 being formed after lamination of the first and second LCP layers 112, 114, it may be formed before the lamination. For instance, Block 306 could also include providing the first LCP body section 72 to include the LCP layer 112 and the second interconnect layer 90 thereon.

After the lamination of the first and second LCP body sections 72, 74, vias or through holes 99 are formed using a laser through the first and second LCP body sections 72, 74 at Block 318 and as illustrated in FIG. 5. In addition, the laser may also be used to clean, mill and redefine the respective gaps in the openings 77 in the second LCP body section 74.

Figure 6:
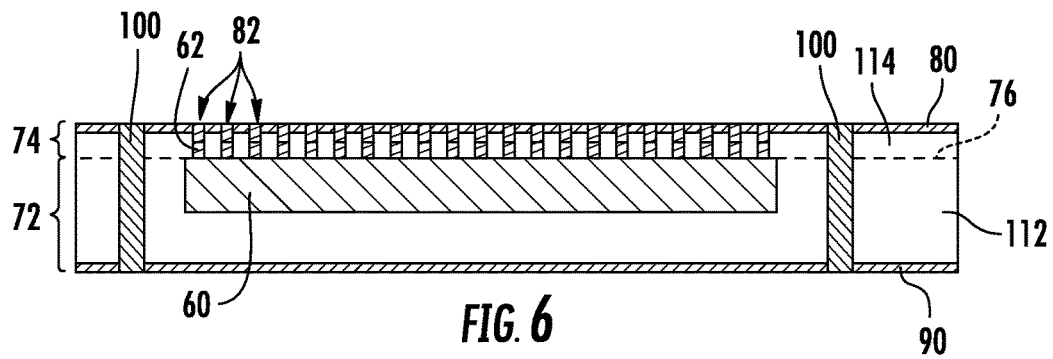
FIG. 6 is a cross-sectional view of the electronic package illustrated in FIG. 2 with the conductive pillars and the conductive vias in place prior to forming the interconnect traces on the first interconnect layer.

At Block 320 and as illustrated in FIG. 6, the conductive bodies 82 are formed in the respective gaps 97 to connect the conductive pillars 62 to the first interconnect layer 80, and conductive vias 100 are formed extending through the first and second LCP body sections 72, 74 to connect the first and second interconnect layers 80, 90. As noted above, the conductive pillars 62 and the first and second interconnect layers 80, 90 are copper. The conductive bodies 82 and the conductive vias 100 are formed using electroplated copper. After the electroplating, interconnect traces 130 as illustrated in FIG. 2 are etch defined to complete the electronic package 50, as readily appreciated by those skilled in the art. The method ends at Block 322.

Many modifications and other embodiments of the invention will come to the mind of one skilled in the art having the benefit of the teachings presented in the foregoing descriptions and the associated drawings. Therefore, it is understood that the invention is not to be limited to the specific embodiments disclosed, and that modifications and embodiments are intended to be included within the scope of the appended claims.

That which is claimed is:

1. A method for making an electronic package comprising:
    forming a liquid crystal polymer (LCP) body surrounding a semiconductor die having a plurality of conductive pillars extending outwardly from an upper surface thereof by joining together a first LCP body section and a second LCP body section at a fused interface;
    the first LCP body section having an upper surface area and a die receiving cavity therein receiving the semiconductor die, with the upper surface area of the first LCP body section being aligned with an upper surface area of the semiconductor die; and
    the second LCP body section having a lower surface area with a plurality of openings therein receiving respective ones of the plurality of conductive pillars, and with the upper surface area of the first LCP body section being joined with the lower surface area of the second LCP body section at the fused interface.

2. The method according to claim 1, wherein the plurality of openings in the second LCP body section leave respective gaps adjacent tops of the conductive pillars.

3. The method according to claim 2, further comprising:
    forming a first interconnect layer on the second LCP body section before joining together the first and second LCP body sections; and
    forming a plurality of conductive bodies in the respective gaps to connect the plurality of conductive pillars to the first interconnect layer.

4. The method according to claim 3, further comprising forming a second interconnect layer on the LCP body on a side thereof opposite the first interconnect layer.

5. The method according to claim 4, further comprising forming a plurality of conductive vias extending through the LCP body to connect the first and second interconnect layers.

6. The method according to claim 3, further comprising cleaning and redefining the respective gaps in the plurality of openings before forming the plurality of conductive bodies.

7. The method according to claim 3, wherein forming the plurality of conductive bodies comprises forming the plurality of conductive bodies using electroplating.

8. The method according to claim 1, further comprising aligning the plurality of openings in the second LCP body section with the plurality of conductive pillars before joining together the first and second LCP body sections.

9. The method according to claim 1, wherein forming the LCP body comprises forming the LCP body to surround the semiconductor die on all sides thereof and to be in contact therewith.

10. The method according to claim 1, wherein forming the LCP body comprises forming the LCP body to laterally surround each of the plurality of conductive pillars and to be in contact therewith.

11. The method according to claim 1, wherein the semiconductor die comprises a radio frequency (RF) integrated circuit.

12. A method for making an electronic package comprising:
    forming a liquid crystal polymer (LCP) body surrounding a semiconductor die having a plurality of conductive pillars extending outwardly from an upper surface thereof by joining together a first LCP body section and a second LCP body section at a planar fused interface, the semiconductor die comprising a radio frequency (RF) integrated circuit;
    the first LCP body section having an upper surface area and a die receiving cavity therein receiving the semiconductor die, with the upper surface area of the first LCP body section being coplanar with an upper surface area of the semiconductor die; and
    the second LCP body section having a lower surface area with a plurality of openings therein receiving respective ones of the plurality of conductive pillars and leaving respective gaps adjacent tops of the conductive pillars, and with the upper surface area of the first LCP body section being joined with the lower surface area of the second LCP body section at the planer fused interface.

13. The method according to claim 12, further comprising:
    forming a first interconnect layer on the second LCP body section before joining together the first and second LCP body sections; and forming a plurality of conductive bodies in the respective gaps to connect the plurality of conductive pillars to the first interconnect layer.

14. The method according to claim 13, further comprising forming a second interconnect layer on the LCP body on a side thereof opposite the first interconnect layer.

15. The method according to claim 14, further comprising forming a plurality of conductive vias extending through the LCP body to connect the first and second interconnect layers.

16. The method according to claim 13, further comprising cleaning and redefining the respective gaps in the plurality of openings before forming the plurality of conductive bodies.

17. The method according to claim 12, further comprising aligning the plurality of openings in the second LCP body section with the plurality of conductive pillars before joining together the first and second LCP body sections.

18. A method for making an electronic package comprising:
    forming a liquid crystal polymer (LCP) body surrounding a semiconductor die having a plurality of conductive pillars extending outwardly from an upper surface thereof by joining together a first LCP body section and a second LCP body section at a planar fused interface;
    the first LCP body section having an upper surface area and a die receiving cavity therein receiving the semiconductor die, with the upper surface area of the first LCP body section being coplanar with an upper surface area of the semiconductor die;
    the second LCP body section having a lower surface area with a plurality of openings therein receiving respective ones of the plurality of conductive pillars and leaving respective gaps adjacent tops of the conductive pillars, and with the upper surface area of the first LCP body section being joined with the lower surface area of the second LCP body section at the planer fused interface;
    forming a first interconnect layer on the second LCP body section before joining together the first and second LCP body sections; and
    forming a plurality of conductive bodies in the respective gaps to connect the plurality of conductive pillars to the first interconnect layer.

19. The method according to claim 18, further comprising forming a second interconnect layer on the LCP body on a side thereof opposite the first interconnect layer.

20. The method according to claim 19, further comprising forming a plurality of conductive vias extending through the LCP body to connect the first and second interconnect layers.

21. The method according to claim 18, further comprising aligning the plurality of openings in the second LCP body section with the plurality of conductive pillars before joining together the first and second LCP body sections.

* * * * *